United States Patent [19]

Redmore et al.

[11] 4,075,291
[45] Feb. 21, 1978

[54] PYROPHOSPHATES

[75] Inventors: Derek Redmore, Ballwin; Benjamin T. Outlaw, Webster Groves; Richard L. Martin, Brentwood, all of Mo.

[73] Assignee: Petrolite Corporation, St. Louis, Mo.

[21] Appl. No.: 649,832

[22] Filed: Jan. 16, 1976

Related U.S. Application Data

[63] Continuation-in-part of Ser. No. 874,713, Nov. 6, 1969, abandoned.

[51] Int. Cl.$^2$ .................... C07F 9/165; C02B 5/06
[52] U.S. Cl. .................... 260/933; 21/2.5 A; 21/2.7 A; 210/58; 252/8.5 C; 252/8.55 D; 252/8.55 E; 252/180; 252/181; 260/950; 260/981
[58] Field of Search .................... 260/933, 988

[56] References Cited

U.S. PATENT DOCUMENTS 3,654,170   4/1972   Woodson et al. ............ 260/988 X

FOREIGN PATENT DOCUMENTS 2,124,145   9/1972   France .................... 260/933

*Primary Examiner*—Anton H. Sutto
*Attorney, Agent, or Firm*—Sidney B. Ring; Hyman F. Glass

[57] ABSTRACT

Pyrophosphates, containing both oxygen and sulfur, of the formula

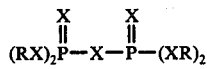

where X is oxygen or sulfur such as those of the formula

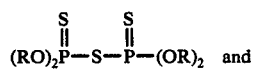 and

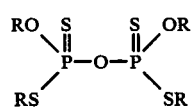

where R is other than a lower alkyl group (i.e. containing less than seven carbon atoms) and preferably a higher alkyl (i.e. at least six carbons), phenol, etc., and most preferably an oxyalkylated radical. Pyrophosphates are prepared by reacting $P_2S_5$ with the appropriate alcohol and continuing the reaction to convert the O,O-disubstituted dithiophosphoric acid initially formed to the pyrophosphate. The resulting product usually contains the O,O-disubstituted dithiophosphoric acid in addition to the pyrophosphate. The pyrophosphate, or mixture of the pyrophosphate with the O,O-disubstituted dithiophosphoric acid, is particularly useful as a corrosion inhibitor in oxygenated and/or aqueous systems as well as for other uses, etc.

8 Claims, No Drawings

PYROPHOSPHATES

This Application is a continuation-in-part of Ser. No. 874,713, filed Nov. 6, 1969, and now abandoned.

One of the most difficult problems in the field of corrosion inhibition is that of preventing and/or inhibiting corrosion in oxygenated aqueous systems such as in water floods, cooling towers, drilling muds, air drilling, auto radiator systems, etc.

Many corrosion inhibitors capable of performing in non-aqueous systems and/or non-oxygenated systems perform poorly in aqueous and/or oxygenated systems (i.e. aerobic systems).

In the application Ser. No. 821,144, filed on May 1, 1969, and now abandoned, of which said application Ser. No. 874,713 is a continuation-in-part, there is described and claimed dithiophosphoric acids and the use thereof as corrosion inhibitors in aqueous and/or oxygenated systems.

Although the reaction of simple alcohols with $P_2S_5$ primarily proceeds according to the following equation $$4ROH + P_2S_5 \longrightarrow 2(RO)_2\overset{S}{\underset{\|}{P}}SH + H_2S ,$$

with minor side reactions, we have discovered that when certain alcohols are reacted, for example higher alkyl alcohols, phenols, oxyalkylated alcohols, etc., side reactions predominate. Thus,

initially formed from such alcohols yields through anhydride formation and/or isomerization pyrophosphates as illustrated in the following equations:

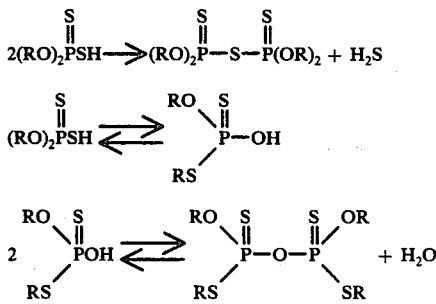

Although the ratio of products will vary with reactants, properties, reaction conditions, etc., a typical reaction product ratio of products formed by reacting an oxyalkylated alcohol with $P_2S_5$ is as follows:

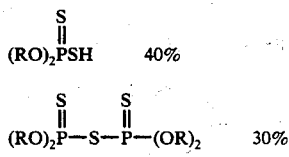

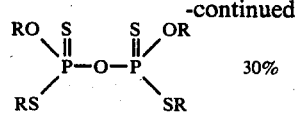

Thus, the major part of the product comprises anhydrides and/or isomerized anhydrides (i.e. pyrophosphates) which are excellent corrosion inhibitors, etc.

The production of pyrophosphates which contain both sulfur and oxygen of the formula

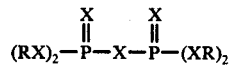

where X = O or S in substantial amounts is unexpected since the reaction of simple alcohols, such as lower alkyl alcohols ROH, with $P_2S_5$ yields little, if any, pyrophosphates. See Houban-Weyl, Phosphorus Compounds, Part II, p. 684, published by Georg Thieme Verlag in 1964. In contrast where the more complex alcohols are reacted, for example, oxyalkylated alcohol such as of the formula $R(OA)_nH$ where R is alkyl, cycloalkyl, alkenyl, aryl, aralkyl, alkaryl, heterocyclic, etc., higher alkyl alcohols such as where R has at least seven carbon atoms, etc., pyrophosphates comprise a substantial part of the resultant reaction product. In general, the yield of pyrophosphate is increased by prolonged heating. Thus, in order to increase the yield of pyrophosphates, in contrast to reaction time of 1 – 3 hours for the dialkyl dithiophosphates, reaction times at elevated temperatures of more than 3 hours, such as 3 – 15 or more hours, enhance the yield of pyrophosphates. The use of vacuum or reduced pressure during this heating period also enhances the yield of pyrophosphates, e.g. 20 mm – 150 mm.

The general procedure for reacting alcohols with $P_2S_5$ to form dithiophosphoric acids is to continue reaction until most of the $P_2S_5$ had dissolved and the evolution of $H_2S$ has subsided. In contrast, the general procedure for preparing the pyrophosphates is to continue the reaction past this point so as to shift the equilibrium in favor of converting the dithiophosphoric acids to the pyrophosphate.

Since the crude reaction products contain 0,0-disubstituted dithiophosphoric acids.

salts of these can also be prepared.

The salts are prepared by the simple neutralization of the acid with a suitable salt-forming base or by double decomposition. The sale moiety may be for example, Cu, Ni, Al, Pb, Hg, Cd, Sn, Zn, Mg, Na, K, $NH_4$, amine, Co, Sr, Ba, etc. These may be prepared from the corresponding oxide, hydroxide, carbonate, sulfide, etc. An alternative to the preparation of salts is to use a simple combination of dithiophosphate with a metal salt such as zinc chloride, zinc sulfate, etc. This allows the use of higher stoichiometric amounts of metal ions to dithiophosphate, such as from 1:1 to 4:1.

It has further been found that the iodide ion added to the dithiophosphate-metal salt combination enhanced the protection such as the addition of one part iodide to 1000 parts thiophosphate in rtios of 1 to 10. Greater or lesser amounts may also be employed.

The alcohols employed to prepare the ester may be oxyalkylated alcohols for example of the formula R(OA)$_n$H where OA is a moiety derived from an alkylene oxide and $n$ is a number for example from about 1 - 100 or more, for example from 1 - 50, such as from 1 - 25, but preferably from 1 - 10.

The alkylene oxides employed herein are 1,2-alkylene oxides of the formula

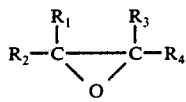

where $R_1$, $R_2$, $R_3$ and $R_4$ are selected by the group consisting of hydrogen, aliphatic, cycloaliphatic, aralkyl, etc. for example ethylene oxide, propylene oxide, butylene oxide, amylene oxide, octylene oxide, styrene oxide, methyl strene oxide, cyclohexene oxide (where $R_1$ and $R_3$ are joined to make a ring), etc.

The alkylene oxide may be added to form homo polymer, stepwise to form block polymers, as mixtures to form heteropolymers or combinations thereof, etc.

For example

R(OEt)$_n$H,

R(OPr)$_n$H,

R(OEt)$_n$(OPr)$_m$H,

R(OPr)$_n$(OEt)$_m$H,

R(OEt—OPr)$_n$H, etc.
mixed

The following examples are presented by way of illustration and not of limitation and not of limitation.

EXAMPLE 1

This example illustrates the reaction of a higher alkanol with P$_2$S$_5$. Dodecyl alcohol (186g; 1.0 mole) was stirred vigorously while phosphorus pentasulfide (55.5g; 0.25 mole) was added at 20°- 50° C. during 1 hour. The reaction temperature was raised to 100°- 105° C. during 1 hour and the pressure reduced to 50 mm. Heating under vacuum was continued for 8 hour at which time no more weight loss was obtained. Yield 229.7g. The product gave following analyses: Sulfur content 12.4%, Acid value 0.86 meg./g.

From these data the composition of the product is approximately

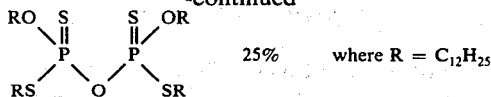 25%  where R = C$_{12}$H$_{25}$

EXAMPLE 2

This example illustrates the use of different reaction conditions for the reactants of Example 1.

Dodecyl alcohol (186g; 1.0 mole) was heated to 90° and stirred gently at this temperature during the addition of P$_2$S$_5$ (55.5g; 0.25 mole) over 1 ½ hours. Heating was continued for 10 hours at 100°-105° C. and a vacuum of 50 mm was then applied for 1 hour. The product was a pale yellow oil. Yield 224g. Product gave analyses: S = 13.5%, Acid value 0.81 meg./g.

The composition calculated from these data is:

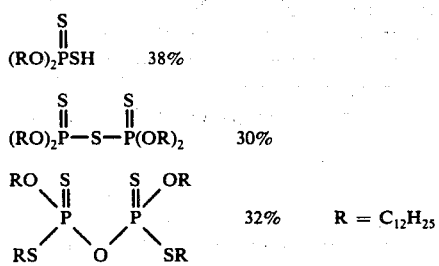

EXAMPLE 3

This example illustrates the reaction of an oxyalkylated alcohol with P$_2$S$_5$.

The alcohol derived from the addition of 1 weight of ethylene oxide to "Alfol" 8 - 10 (576g; 2 mole) was stirred at 25° - 40° while P$_2$S$_5$ (111g; 0.5 mole) was added during 2 hours. The reaction was heated to 105°-109° at a pressure of 70 mm for 9½ hours. Upon cooling the product, 657g. was obtained as a pale yellow liquid. Sulfur analysis, 9.06%; phosphorus, 4.77%, acid value 0.62 meg/g.

The composition from these data is approximately:

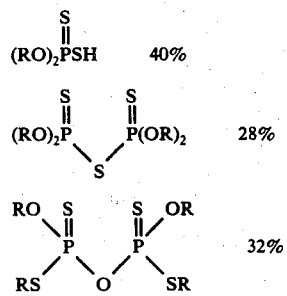

R derived for "Alfol" 8 - 10, i.e.
CH$_3$(CH$_2$)$_{7-9}$OH + 3.23 EtO

The following specific mixture is obtained by the reaction of Example 3:

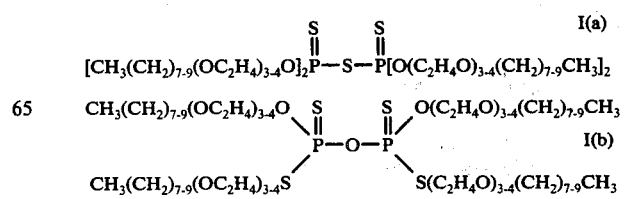

-continued

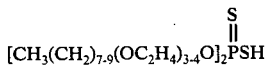

in the ratio of I(a) to I(b) to II of 28% to 32% to 40%.

In order to avoid repetitive details additional illustrative examples are tabulated below:

|  | Alcohol | Procedure |
| --- | --- | --- |
| Example 4 | "Alfol"8–10 + 1 wt. EtO | Example 2 |
| Example 5 | "Alfol"8–10 + 2 wt. EtO | Example 1 |
| Example 6 | P-nonylphenol + 1.2 wt. Eto | Example 1 |
| Example 7 | "Alfol"14 + 2 wt. EtO $CH_3(CH_2)_{13}OH$ | Example 1 |
| Example 8 | "Alfol"14 + 2 wt. EtO $CH_3(CH_2)_{13}OH$ | Example 2 |

In general, the alcohols which react with $P_2S_5$ to form pyrophosphates are higher alkanols (i.e. having at least 7 carbons), phenols for example alkyl phenols were each alkyl group has from about 1 – 18 or more carbon, polyalkyl phenols, etc., alkylaralkyl alcohols

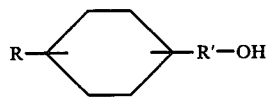

for example, nonylpheylmethanol, etc., cycloalkanols such as cyclohexyl alcohol, methyl cyclohexyl alcohol, etc., oxyalkylated alcohols $R(OA)_nH$; unsubstituted alcohols; heterocyclic alcohols; polyfunctional alcohols, etc. Stated another way the present process of forming pyrophosphates can be achieved by converting the O,O-disubstituted thiophosphate form to the pyrophosphate form using heat, vacuum, time, etc., to shift the equilibrium in the direction of the pyrophosphates. It is more readily carried out with the more complex alcohol as contrasted to the more simple alcohol such as lower alkanols.

USE IN BRINES

This phase of the invention relates to the prevention of corrosion in systems containing a corrosive aqueous medium, and most particularly in systems containing brines.

More particularly, this invention relates to the prevention of corrosion in the secondary recovery of petroleum by water flooding and in the disposal of waste water and brine from oil and gas wells. Still more particularly, this invention relates to a process of preventing corrosion in water flooding and in the disposal of waste water and brine from oil and gas walls which is characterized by injecting into an underground formation an aqueous solution containing minor amounts of compositions of this invention, in sufficient amounts to prevent the corrosion of metals employed in such operation. This invention also relates to corrosion inhibited brine solutions of these compounds.

When an oil well ceases to flow by the natural pressure in the formula and/or substantial quantities of oil can no longer be obtained by the usual pumping methods, various processes are sometimes used for the treatment of the oil-bearing formation in order to increase the flow of the oil. The processes are usually described as secondary recovery processes. One such process which is used quite frequently is the water flooding process wherein water is pumped under pressure into what is called an "injection well" and oil, along with quantities of water, that have been displaced from the formation, are pumped out of an adjacent well usually referred to as a "producing well". The oil which is pumped from the producing well is then separating from the water that has been pumped from the producing well and the water is pumped to a storage reservoir from which it can again be pumped into the injection well. Supplementary water from other sources may also be used in conjunction with the producing water. When the storage reservoir is open to the atmosphere and the oil is subject to aeration this type of water flooding system is referred to herein as an "open water flooding system." If the water is recirculated in a closed system without substantial aeration, the secondary recovery method is referred to herein as a "closed water flooding system."

Because of the corrosive nature of oil field brines, to economically produce oil by water flooding, it is necessary to prevent or reduce corrosion since corrosion increases the cost thereof by making it necessary to repair and replace such equipment at frequent intervals.

We have now discovered a method of preventing corrosion in systems containing a corrosive aqueous media, and most particularly in systems containing brines, which is characterized by employing the compositions of this invention.

We have also discovered an improved process of protecting from corrosion metallic equipment employed in secondary oil recovery by water flooding such as injection wells, transmission lines, filters, meters, storage tanks, and other metallic implements employed therein and particularly those containing iron, steel, and ferrous alloys, such process being characterized by employing in water flood operation the compositions of this invention.

This phase of the invention then is particularly concerned with preventing corrosion in a water flooding process characterized by the flooding medium containing an aqueous or an oil field brine solution of these compounds.

In many oil fields large volumes of water are produced and must be disposed of where water flooding operations are not in use or where water flooding operations cannot handle the amount of produced water. Most States have laws restricting pollution of streams and land with produced waters, and oil producers must then find some method of disposing of the waste produced salt water. In many instances therefore, the salt water is disposed by by injecting the water into permeable low pressure strata below the fresh water level. The formation into which the water is injected is not the oil producing formation and this type of disposal is defined as salt water disposal or waste water disposal. The problems of corrosion of equipment are analogous to those encountered in the secondary recovery operation by water flooding.

The compositions of this invention can also be used in such water disposal wells thus providing a simple and economical method of solving the corrosion problems encountered in disposing of unwanted water.

Water flood and waste disposal operations are too well known to require further elaboration. In essence, in the present process, the flooding operation is effected in the conventional manner except that the flooding medium contains a minor amount of the reducing compound, sufficient to prevent corrosion, in concentrations of about 10 p.p.m. to 10,000 p.p.m., or more, for example, about 50 to 5000 p.p.m., but preferably about 15 to 1,500 p.p.m. The upper limiting amount of the compounds is determined by economic considerations. Since the success of a water flooding operation manifestly depends upon its total cost being less than the value of the additional oil recovered from the oil reservoir, it is quite important to use as little as possible of these compounds consistent with optimum corrosion inhibition. Optimum performance is generally obtained employing about 100 p.p.m. Since these compounds are themselves inexpensive and are used in low concentrations, they enhance the success of a flood operation by lowering the cost thereof.

In addition, these compounds are not sensitive to oxygen content of the water and these are effective corrosion inhibitors in both open water flooding systems and closed water flooding systems.

While the flooding medium employed in accordance with the present invention contains water or oil field brine and the compounds, the medium may also contain other materials. For example, the flooding medium may also contain other agents such as surface active agents or detergents which aid in wetting throughout the system and also promote the desorption of residual oil from the formation, sequestering agents which prevent the deposition of calcium and/or magnesium compounds in the interstices of the formation, bactericides which prevent the formation from becoming plugged through bacterial growth, tracers, etc. Similarly, they may be employed in conjunction with any of the operating techniques commonly employed in water flooding and water disposal processes, for example five spot flooding, peripheral flooding, etc., and in conjunction with other secondary recovery methods.

Corrosion tests were made using sand blasted 1020 mild steel coupons monitored by a polyarization resistance meter, a PAIR instrument described in U.S. Pat. No. 3,406,101. These tests were made in cylindrical containers of 1500 cc volume with provision for constant stirring by means of a motor driven impeller. A thermostatically controlled immersion heater maintained an average temperature of 75° C. and an air inlet kept the fluids constantly saturated with air. Between each test the cylinder was cleaned with steam, benzene, acetone and thoroughly washed with clean water. Results of these corrosion tests made in various aqueous environments are shown in the following Table.

Protection is calculated in the usual manner from corrosion rate ($R_1$) of fluids without inhibitor and corrosion rate ($R_2$) in presence of particular inhibitor according to the formula $$\frac{R_1 - R_2}{R_1} \times 100 = \text{Percent protection}.$$

TABLE A

Corrosion results in Laboratory brine
(4.2% NaCl, 1.7% Mg Cl$_2$, 0.15 CaCl$_2$, 0.09% Na$_2$SO$_4$ pH 6.0)

| Product of Example | Concentration | Additives | Protection at 24 hrs. |
|---|---|---|---|
| 1 | 1000 ppm | — | 90% |
| 2 | 1000 ppm | — | 80% |
| 3 | 1000 ppm | — | 92% |
| 7 | 1000 ppm | — | 81% |
| Mercapto-benzothiazole Commercial | 1000 ppm | — | 30% |
| imidazoline | 1000 ppm | — | 5% |

USE IN FLUIDS FOR DRILLING WELLS

This phase of the invention relates to the use of the compounds of this invention as corrosion inhibitors in producing an improved drilling fluid useful in drilling oil and gas wells.

Fluids commonly used for the drilling of oil and gas wells are of two general types: water-base drilling fluids comprising, for example, a clay suspended in water, and oil-base drilling fluids comprising, for example, a clay or calcium carbonate suspended in mineral oil.

A third type of drilling fluid which has recently been developed, is one of oil-in-water or water-in-oil emulsion, for example, emulsions of mineral oil in water or water in mineral oil formed by means of emulsifiers such as sulfuric acid; Turkey-red oil; soaps of fatty acids, for example, sodium oleate, emulsoid colloids, for example starch, sodium alginate, etc. Varying amounts of finely divided clay, silica, calcium carbonate, blown asphalt and other materials may be added to these emulsions to improve their properties and control their weight.

We have now discovered that the compositions of this invention can be employed as a corrosion inhibitor in drilling fluids as illustrated in the following Table. These are illustrative of high brine drilling fluids which are extremely corrosive.

TABLE B

Corrosion results in typical brine drilling mud
(24% CaCl$_2$, 7% NaCl, 10 lb./gal., pH 6.0)

| Product of Example | Concentration | Additive | Protection at 24 hrs. |
|---|---|---|---|
| 1 | 1000 ppm | — | 51% |
| 1 | 1000 ppm | ZnCl$_2$, 250 ppm as zinc ion | 78% |
| 3 | 1000 ppm | — | 72% |
| 3 | 1000 ppm | ZnCl$_2$, 250 ppm as zinc ion | 80% |
| 3 | 1000 ppm | ZnCl$_2$, 250 ppm as zinc ion I$^-$ ion 90 ppm | 85% |
| Commercial imidazoline | 1000 ppm | — | 7% |

USE IN AIR DRILLING

It has long been conventional practice in drilling deep bore holes to circulate a drilling mud down through the drill stem and up through the bore hole between the wall of the bore hole and the drill stem for the removal of chips or cuttings from the bore hole and to provide support for the wall of the bore hole. More recently, in the drilling of holes in which wall support provided by drilling mud is not employed, drilling has been carried out with the use of air for chip removal. Such drilling is not only normally faster than mud drilling but is indispensable in areas where the supply of water is limited or when drilling through cavernous formations into which the drilling mud flows and becomes lost.

The increasing popularity of air or gas drilling has come about not only because this method of drilling is frequently faster, as noted above, but for the additional reasons that the drill bits last longer, the provision and handling of water under wide ranges of temperature conditions is avoided, boring samples are easily observed when they are not mixed with mud, and there is no loss involved as in the case of mud drilling when drilling through cavernous formations. Furthermore, prompt removal of water entering the hole maintains a dry hole and the likelihood of wall collapse is thereby reduced.

In a typical air drilling operation there may be provided, for example, an up-flow of air in the bore hole having a velocity of the order of 3,000 feet per minute. This flow of air upwardly through the bore hole, which is produced by air pumped downwardly through the drill stem, provides adequate removal of cuttings. The air is delivered to the drill stem at pressures of 20 to 60 lbs. per square inch and for dewatering or for breaking obstructions, as will be hereinafter described, the pressures may be increased to 180 to 200 lbs. or more per square inch.

Air drilling operations are frequently hampered by the inflow of water into the bore hole when the drill bit is penetrating a water bearing stratum or when the bore hole has passed through a water bearing stratum that has not been caused. Normally, if drilling proceeds uninterruptedly both before and during penetration into a water bearing stratum, the flow of air is sufficient to blow the water out of the bore hole along with the cuttings and drilling dirt. There are however, two major problems encountered in air drilling when water is entering the bore hole. The first problem occurs when there is a small inflow of water sufficient to cause a dampening of the cuttings which, under certain condition, will then ball-up, clogging and sometimes jamming the drill bit. The second problem is encountered when there is a substantial amount of water remaining in the bottom of the bore hole during drilling causing a sloughing of the side wall of the bore hole. This latter condition may arise even though the water entering the bore hole is being blown out of the hole as fast as it enters. If there is a substantial inflow of water or if there is a substantial flow of water past a region of the bore hole susceptible to this condition, the water passing that region of the bore hole may cause a sloughing of the side wall.

The addition of foam forming materials to the air flow when air drilling is employed in conjunction with sufficient water to provide foaming gives rise to numerous advantages in drilling operations. The water may be introduced either through a water bearing stratum being penetrated by the drill bit or, alternatively, if the hole is dry, water may be introduced from the surface of the earth through the drill stem in conjunction with the delivery of compressed air and foam forming material through the drill stem to the drill bit. In either case the water may be said to be existing in the bore hole, and drilling operations are described in U.S. Pat. No. 3,130,798.

The compositions of this invention can be employed as a corrosion inhibitor in a drilling system.

The compositions of this invention may also be added to other aqueous and/or oxygenated systems such as steam generating systems, water circulating systems such as in cooling towers, in automobile radiators, in diesel locomotive engines, in boiler water, sea-water ship ballast, etc.

The amount of the compositions of the invention to be employed as a corrosion inhibitor can vary widely depending upon particular compounds, the particular system, the amounts of oxygen present, etc. We may employ concentrations of from about 0.5 to 5,000 p.p.m., such as from about 4 to 4,000 p.p.m., for example from about 20 to 2,000 p.p.m., but preferably from about 100 to 1,000 p.p.m. The optimum amount, to be determined in each instance, which will depend on function and economics, can be lesser or greater than the above amounts under proper conditions.

USE IN ANTIFREEZE SYSTEMS

The following table shows the utility of the compositions of this invention in antifreeze formulations and their superiority with a presently marketed inhibited antifreeze.

Use as corrosion inhibitor for cooling systems such as aqueous glycol antifreeze.

These corrosion tests were carried as described for aqueous brines using appropriate metals. These tests were performed at 88° C.

The following inhibitor formulations were prepared:

|  | Parts by Weight |
|---|---|
| Formulation A: | |
| Compound of Example 1 | 1 |
| Borax | 8 |
| Mercaptobenzothiazole | 1 |
| Formulation B: | |
| Compound of Example 1 | 3 |
| Borax | 16 |
| Mercaptobenzothiazole | 1 |
| Formulation C: | |
| Compound of Example 1 | 9 |
| Borax | 40 |
| Mercaptobenzothiazole | 1 |
| Formulation D: | |
| Compound of Example 3 | 3 |
| Borax | 16 |
| Mercaptobenzothiazole | 1 |

TABLE C

| Compound | Concentration | Metal | Corrosion Rate | Protection |
|---|---|---|---|---|
| Blank | — | Cast Iron | 2.1 mpy* | — |
| Formulation B | 5000 ppm | Cast Iron | 1.2 mpy | 42% |
| Commercially Inhibited | 5000 ppm | Cast Iron | 1.8 mpy | 15% |
| Blank | — | Aluminum | 5.1 mpy | — |
| Formulation A | 5000 ppm | Aluminum | 2.7 mpy | 52% |
| Formulation D | 5000 ppm | Aluminum | 2.3 mpy | 60% |
| Commercially Inhibited | 5000 ppm | Aluminum | 2.5 mpy | 56% |
| Blank | — | Copper | 2.2 mpy | — |
| Formulation A | 5000 ppm | Copper | 0.2 mpy | 90% |
| Formulation B | 5000 ppm | Copper | 0.3 mpy | 85% |
| Commercially Inhibited | 5000 ppm | Copper | 0.54 mpy | 72% |
| Blank | — | Solder | 0.97 mpy | — |
| Formulation A | 5000 ppm | Solder | 0.34 mpy | 65% |
| Commercially Inhibited | 5000 ppm | Solder | 0.84 mpy | 15% |

*mpy—mils per year

In summary, the present invention relates to the pyrophosphates, alone or in combination with dithiophosphates or salts thereof (also in combination with iodide) and to the use as corrosion inhibitors in a wide variety of aqueous and/or oxygenated systems. The pyrophosphates may be employed as the crude product resulting from the reaction of the alcohol with $P_2S_5$ or may be separated from the reaction mixture.

As is quite evident, new pyrophosphates will be constantly developed which could be useful in our invention. It is, therefore, not only impossible to attempt a comprehensive catalogue of such compositions, but to attempt to describe the invention in its broader aspects in terms of specific chemical names used would be too voluminous and unnecessary since one skilled in the art could be following the description of the invention herein select a useful pyrophosphate. This invention lies in the use of suitable pyrophosphates in conjunction with suitable salts where appropriate as corrosion inhibitors in aqueous and/or oxygenated systems and their individual compositions are important only in the sense that their properties can affect this function. To precisely define each specific useful pyrophosphate and aqueous system in light of the present disclosure would merely call for knowledge within the skill of the art in a manner analogous to a mechanical engineer who prescribes in the construction of a machine the proper materials and the proper dimensions thereof. From the description in this specification and with the knowledge of a chemist, one will know or deduce with confidence the applicability of specific pyrophosphates suitable for this invention by applying them in the process set forth herein. In analogy to the case of a machine, wherein the use of certain materials of construction or dimensions of part would lead to no practical useful result, various materials will be rejected as inapplicable where others would be operative. We can obviously assume that no one will wish to use a useless pyrophosphate nor will be misled because it is possible to misapply the teachings of the present disclosure to do so. Thus, any pyrophosphate or mixtures containing them that can perform the function stated herein can be employed.

We claim:

1. A mixture of compounds comprising
I. a mixture of different compounds, each having the formula

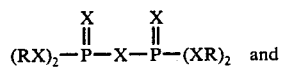 and

II. a compound or mixture of compounds, each having the formula

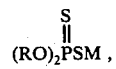, where R is an alkyl or oxyalkylated alkyl radical having at least 7 carbon atoms, X is oxygen or sulfur, each of said compounds in I containing both oxygen and sulfur, and the compound or mixture of compounds I being the major component of said mixture, M is hydrogen or a metal, said mixture of compounds I and II being prepared by an alcohol or a mixture of alcohols with $P_2S_5$ first to form O,O-disubstituted dithiophosphric acid or a mixture thereof until most of the $P_2S_5$ has dissolved and the evolution of $H_2S$ has subsided and then continuing the reaction to shift the equilibrium in favor of converting dithiphosphoric acid or a mixture thereof to the pyrophosphates, with the proviso that, where M is a metal, dithiophosphoric acid or a mixture thereof is neutralized with a salt-forming base or by double decomposition.

2. The mixture of compounds of claim 1 where R is an oxyalkylated radical of the formula $R'(OA)_n$, $R'$ being alkyl, OA being alkylene oxide and $n$ being greater than zero.

3. The mixture of compounds of claim 2 wherein $n$ is about 1 to 10 and alkylene oxide is ethylene oxide, or propylene oxide or a mixture of ethylene oxide and propylene oxide.

4. The mixture of compounds of claim 1 and I is a mixture of different compounds having the formulae

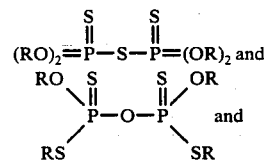

II is a compound or a mixture of compounds each having the formula

and the R's have the same meaning as in claim 1 and may be the same or different.

5. The mixture of compounds of claim 4 wherein R is an oxyalkylated radical of the formula $R'(OA)_n$, $R'$ being $CH_3(CH_2)_{7-9}$, OA being ethylene oxide and $n$ being approximately 3.

6. The mixture of compounds of claim 4 where R is an oxyalkylated radical of the formula $R'(OA)_n$, $R'$ being alkyl, OA being ethylene oxide, propylene oxide or a mixture of ethylene oxide and propylene oxide and $n$ being about 1 to 10.

7. The mixture of compounds of claim 5 where I is $$(CH_3(CH_2)_{7-9}(OC_2H_4)_{3-4}O)_2 \overset{S}{\underset{\|}{P}}-S\overset{S}{\underset{\|}{P}}(O(C_2H_4O)_{3-4}(CH_2)_{7-9}CH_3)_2 \quad \text{(a)}$$

$$\begin{array}{c} CH_3(CH_2)_{7-9}(OC_2H_4)_{3-4}-O \\ CH_3(CH_2)_{7-9}(OC_2H_4)_{3-4}-S \end{array} \overset{S}{\underset{\|}{P}}-O\overset{S}{\underset{\|}{P}} \begin{array}{c} O(C_2H_4O)_{3-4}(CH_2)_{7-9}CH_3 \\ S(C_2H_4O)_{3-4}(CH_2)_{7-9}CH_3 \end{array} \quad \text{(b)}$$

and II is $$(CH_3(CH_2)_{7-9}(OC_2H_4)_{3-4}O)_2 \overset{S}{\underset{\|}{P}}SH.$$

8. The mixture of compounds of claim 7 where the product ratio of I(a) to I(b) to II is approximately 28% to 32% to 40%.

* * * * *